United States Patent
Ohtsuki et al.

(10) Patent No.: US 9,481,710 B2
(45) Date of Patent: Nov. 1, 2016

(54) EVALUATION PEPTIDE FOR USE IN QUANTIFICATION OF PROTEIN USING MASS SPECTROMETER, ARTIFICIAL STANDARD PROTEIN, AND METHOD FOR QUANTIFYING PROTEIN

(75) Inventors: Sumio Ohtsuki, Miyagi (JP); Junichi Kamiie, Kanagawa (JP); Tetsuya Terasaki, Miyagi (JP)

(73) Assignee: Tohoku University, Miyagi (JP)

( * ) Notice: Subject to any disclaimer, the term of this patent is extended or adjusted under 35 U.S.C. 154(b) by 878 days.

(21) Appl. No.: 13/202,474

(22) PCT Filed: Jan. 27, 2010

(86) PCT No.: PCT/JP2010/000446
§ 371 (c)(1),
(2), (4) Date: Aug. 19, 2011

(87) PCT Pub. No.: WO2010/095365
PCT Pub. Date: Aug. 26, 2010

(65) Prior Publication Data
US 2012/0021446 A1 Jan. 26, 2012

(30) Foreign Application Priority Data

Feb. 23, 2009 (JP) .................. 2009-039937

(51) Int. Cl.
| | |
|---|---|
| C12Q 1/37 | (2006.01) |
| A61K 38/04 | (2006.01) |
| C07K 5/00 | (2006.01) |
| C07K 7/00 | (2006.01) |
| C07K 16/00 | (2006.01) |
| C07K 17/00 | (2006.01) |
| C07K 7/06 | (2006.01) |
| C07K 7/08 | (2006.01) |
| G01N 33/68 | (2006.01) |
| H01J 49/00 | (2006.01) |

(52) U.S. Cl.
CPC . C07K 7/06 (2013.01); C07K 7/08 (2013.01); G01N 33/6848 (2013.01); H01J 49/00 (2013.01)

(58) Field of Classification Search
None
See application file for complete search history.

(56) References Cited

U.S. PATENT DOCUMENTS

| | | | | |
|---|---|---|---|---|
| 6,824,981 | B2 * | 11/2004 | Chait | C07K 1/047 435/252.3 |
| 2006/0211077 | A1 * | 9/2006 | Abel et al. | 435/23 |

FOREIGN PATENT DOCUMENTS

| | | |
|---|---|---|
| EP | 1 686 372 | 8/2006 |
| EP | 1953542 A1 | 8/2008 |
| EP | 2 098 859 | 9/2009 |
| JP | 2004-028993 | 1/2004 |
| JP | 2004-077276 | 3/2004 |
| JP | 2004-533610 | 11/2004 |
| JP | 2008-251212 | 10/2008 |
| WO | WO 03040165 | * 5/2003 |
| WO | WO 03/046148 | 6/2003 |
| WO | WO 2005/116660 | 12/2005 |
| WO | WO 2007/055116 | 5/2007 |
| WO | WO 2008/135756 | 11/2008 |

OTHER PUBLICATIONS

Peptide cutter, URL: http://web.expasy.org/cgi-bin/peptide_cutter/peptidecutter.pl?enzyme=Pn2;protein=EPGPIAPSTNSSPVLK;cleave_number=all;cleave_exactly=;cleave_range_min=0;cleave_range_max=16;block_size=60;alphtable=alphtable;seq_table=;cleavage_map=cleavage_map, accessed online Jun. 19, 2014.*
Ma et al. Protein Structure and Folding: Mass Spectrometric Characterization of Full-Length Rat Selenoprotein P and Three Isoforms Shortened at the C Terminus. JBC, 2002. vol. 277, No. 15, pp. 12749-12754.*
Winter, Minimally permutated peptide analogs as internal standards for relative and absolute quantification of peptides and proteins. Proteomics 2010, vol. 10, pp. 1510-1514.*
Breibeck et al. PAS-cal: a Generic Recombinant Peptide Calibration Standard for Mass Spectrometry, JASM, 2014, vol. 25, pp. 1489-1497.*
ExPASy—PeptideCutter for GFPVRPQVLK, http://web.expasy.org/cgi-bin/peptide_cutter/peptidecutter.pl, accessed online Mar. 3, 2015, 1 page.*
ExPASy—PeptideCutter for PGSQPKTK, http://web.expasy.org/cgi-bin/peptide_cutter/peptidecutter.pl, accessed online Mar. 3, 2015, 1 page.*
ExPASy—PeptideCutter for PPGFSPFR, http://web.expasy.org/cgi-bin/peptide_cutter/peptidecutter.pl, accessed online Mar. 6, 2015, 1 page.*
Gerber et al. Absolute quantification of proteins and phosphoproteins from cell lysates by tandem MS. PNAS, Jun. 10, 2003. vol. 100, No. 12, pp. 6940-6945.*

(Continued)

*Primary Examiner* — Marcela M Cordero Garcia
(74) *Attorney, Agent, or Firm* — Margaret Brivanlou; King & Spalding LLP

(57) ABSTRACT

Disclosed is an evaluation peptide for evaluating the efficiency of a pretreatment in the quantification of a protein using a mass spectrometer, having high reliability and high general versatility. Also disclosed is an artificial standard protein comprising the evaluation peptide. Further disclosed is a method for quantifying a protein utilizing the artificial standard protein. Specifically disclosed is a method for selecting a peptide which consists of an amino acid sequence not agreeing with that in a naturally occurring protein and a variant thereof and capable of being detected by mass spectrometry and which has an amino acid that can be recognized by a protein-digesting enzyme, and using the peptide as an evaluation peptide for use in the quantification of a protein by a mass spectrometer.

6 Claims, 10 Drawing Sheets

(56) References Cited

OTHER PUBLICATIONS

Tschesche et al. C-Terminal-Sequence Determination by Carboxypeptidase C from Orange Leaves. Eur J Biochem, 1972. vol. 26, p. 33-36.*

Tohoku University, Extended European Search Report issued in European Patent No. 2400295 dated Aug. 30, 2012, 9 pages.

Beynon et al., "Multiplexed Absolute Quantification in Proteomics Using Artificial QCAT Proteins of Concatenated Signature Peptides," Nature Methods, 2, pp. 587-589, 2005.

Dupuis et al., Protein Standard Absolute Quantification (PSAQ) for Improved Investigation of Staphylococcal Food Poisoning Outbreaks, 2008, 8, pp. 463-4636, Proteomics.

Kito et al., "Peptide Renketsugata Hyojun Busshitsu to Shitsuryo Bunseki (PCS-MS-ho) o Mochiita Tanpakushitsu no Zettai Teiryo Bunseki," Journal of Japanese Biochemical Society, pp. 4T25-2, 2008.

Kito et al., "A Synthetic Protein Approach Toward Accurate Mass Spectrometric Quantification of Component Stoichiometry of Multiprotein Complexes," Journal of Proteome Research, 6, pp. 792-800, 2007.

Sakai et al., "LC-MS/MS o Mochiita Zettai Teiryoho no Hyokayo Recombinant Reference Tanpakushitsu no Hatsugen to Seisei," 128th Annual Meeting of the Pharmaceutical Society of Japan, p. 141, Mar. 5, 2008.

International Search Report from PCT/JP2010/000446 dated Apr. 27, 2010.

Kito et al., "Peptide Renketsugata Hyojun Busshitsu to Shitsuryo Bunseki (PCS-MS-ho) o Mochiita Tanpakushitsu no Zettai Teiryo Bunseki," Journal of Japanese Biochemical Society, pp. 4T25-2, 2008, English Translation.

Sakai et al., "LC-MS/MS o Mochiita Zettai Teiryoho no Kyokayo Recombinant Reference Tanpakushitsu no Hatsugen to Seisei," 128th Annual Meeting of the Pharmaceutical Society of Japan, p. 141, Mar. 5, 2008, English Translation.

Kawakami, H. et al., "Simultaneous Absolute Quantification of 11 Cytochrome P450 Isoforms in Human Liver Microsomes by Liquid Chromatography Tandem Mass Spectrometry with In Silico Target Peptide Selection," J. Pharmaceutical Sciences, vol. 100, No. 1, Jan. 2011, pp. 341-352.

Tohoku University (Applicant), Communication pursuant to Article 94(3) EPC issued for European Patent Application No. 10 743 497.9, Aug. 20, 2015, 8 pages.

Harald Tschesche et al., "C-Terminal-Sequence Determination by Carboxypeptidase C from Orange Leaves", Eur. J. Biochem., vol. 26, pp. 33-36, 1972.

European Patent Office "Communication Pursuant to Article 94(3) EPC", mailed Apr. 1, 2015, for corresponding EP App. No. EP10743497.9 (4 sheets).

* cited by examiner

Figure 3

AMINO ACID SEQUENCE OF PREPARED ARTIFICIAL STANDARD PROTEIN

MAHHHHHHSAALEVLFQGPGYQDPNSKVGAPGVPALKN (SEQ ID NO: 5)
WHQAWHECARHDQQLVTIESADKNNAIIDLVKRVVGKSH
NLWLGGNDEYSSSRDYGRPFFWSPTGQAFSFAYWSEN
NPDNYKHQEHCVHRQIGDPTVPSGVKVPLGQGAKHAKQ
SLRDAPGSGLKQNATQIAIQQIMENHEKKIRDLKNVAPAG
PTLKVDKVGAPGVPALKNWHQAWHECARHDQQLVTIES
ADKNNAIIDLVKRVVGKSHNLWLGGNDEYSSSRDYGRPF
FWSPTGQAFSFAYWSENNPDNYKHQEHCVHRQIGDPT
VPSGVKVPLGQGAKHAKQSLRDAPGSGLKQNATQIAIQ
QIMENHEKKIRDLKNVAPAGPTLK

VGAPGVPAL*K → Probe peptide 1 (SEQ ID NO: 1)
QIGDPTVPSGV*K → Probe peptide 2 (SEQ ID NO: 2)
DAPGSGL*K → Probe peptide 3 (SEQ ID NO: 3)
NVAPAGPTL*K → Probe peptide 4 (SEQ ID NO: 4)

*is labeled area at Isotope labeled peptide

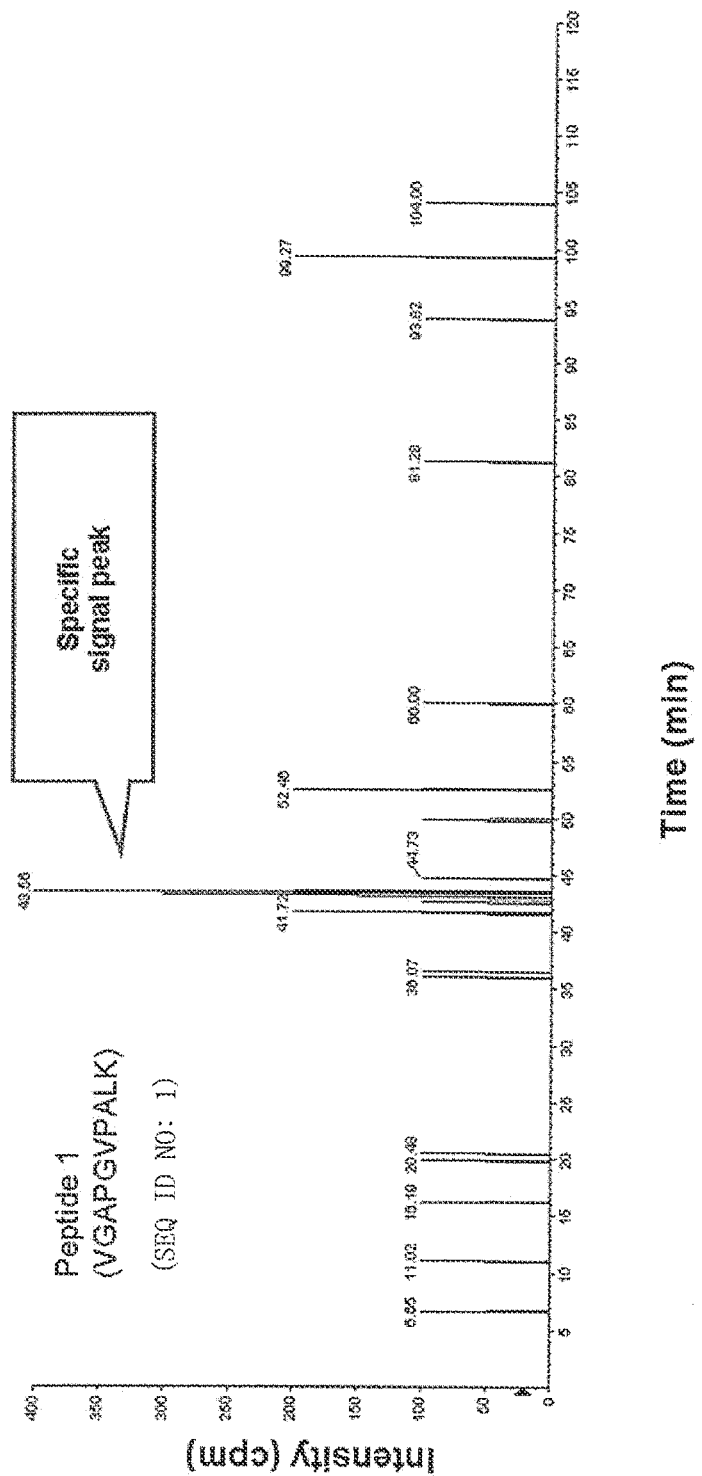

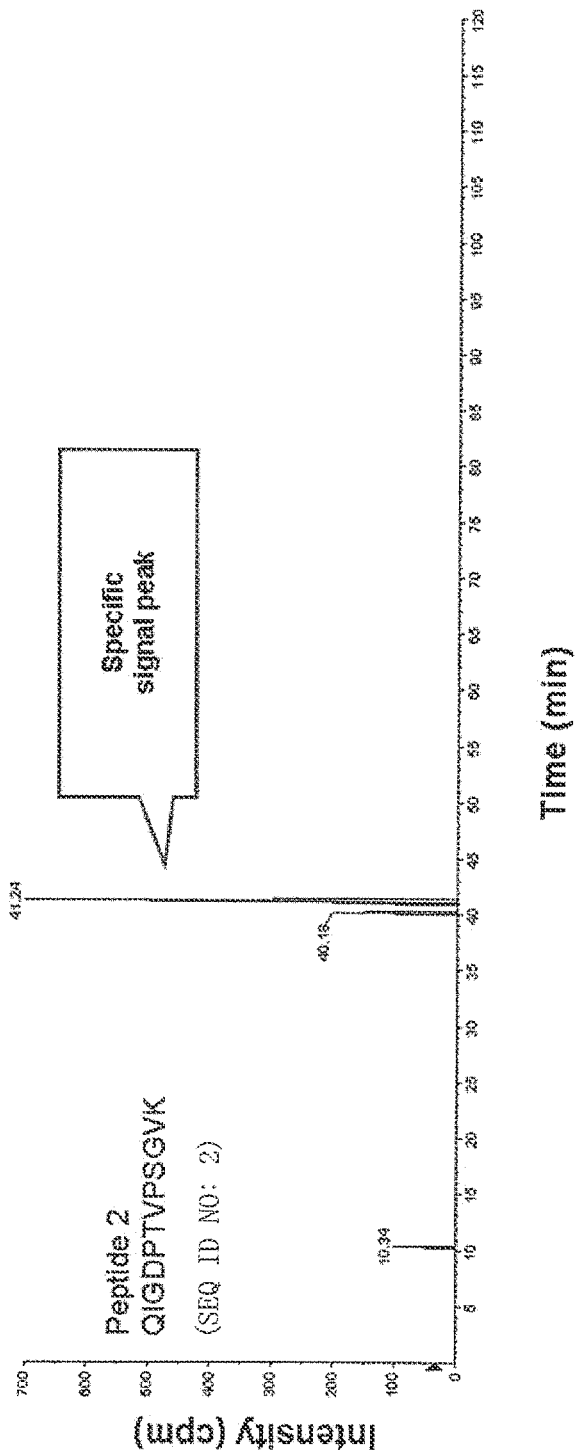

EVALUATION PEPTIDE FOR USE IN QUANTIFICATION OF PROTEIN USING MASS SPECTROMETER, ARTIFICIAL STANDARD PROTEIN, AND METHOD FOR QUANTIFYING PROTEIN

TECHNICAL FIELD

The present invention relates to an evaluation peptide for evaluating the efficacy of a pretreatment in the quantification of a protein using mass spectrometry, an artificial standard protein comprising the peptide, and a method for quantifying a protein using the artificial standard protein. It is preferable to incorporate 2 or more of each of 2 types or more of evaluation peptides in the artificial standard protein, and it is more preferable to further incorporate two or more cysteines therein.

According to the protein quantification method of the present invention, a certain amount of the artificial standard protein of the present invention can be added to a protein sample before pretreatment, followed by performing pretreatment and quantifying the evaluation peptide by mass spectrometry to evaluate the efficacy of the pretreatment from its quantitative value.

BACKGROUND ART

In recent years, the progress of mass spectrometry has been striking and this method has been studied and utilized for the purpose of the detection and measurement of various biological materials. As mass spectrometers, mass spectrometers with various functions have been developed which include a mass spectrometer using electrosprayionization, a mass spectrometer having liquid chromatography-mass spectrometry (LC-MS), and a MS/MS spectrum or tandem mass spectrum in which two spectrometers are connected; a combination of these functions is utilized for the detection, measurement and quantification of biological materials (Patent Documents 1 to 3).

A technique for exhaustively analyzing a protein using a mass spectrometer is called proteomics. A protein is a macromolecule and has a three dimensional structure: thus, it is not suitable for exhaustive separation by liquid chromatography and analysis using a mass spectrometer. Therefore, generally, a protein is denatured, modified, precipitated, and then cut into peptides using a protein-digesting enzyme such as trypsin, and the peptides are separated by liquid chromatography and analyzed using a mass spectrometer. The digested peptide fragments can be identified to identify a protein present in a protein sample and a digested peptide fragment can be further quantified to quantify the expression level of a target protein in the protein sample.

The inventors have already invented methods for exhaustively and simultaneously quantifying the absolute expression levels of a membrane protein and a metabolizing enzyme using a mass spectrometer (Patent Documents 4 and 5). For conventional proteomics intended for identification, the efficiency of a pretreatment such as denaturation, modification, precipitation or digestion has presented little problem although it affects sensitivity. However, for the quantitative methods of the inventors, a sufficient pretreatment forms a precondition because the quantitative value of a targeted digested peptide is used as the quantitative value of a target protein; the quality of the efficiency of the pretreatment greatly influences the accuracy and reliability of the quantitative value. Thus, it is essential for the quantification of a protein using mass spectrometry to evaluate the efficiency of the pretreatment for each sample to confirm that the pretreatment has taken place sufficiently.

Previously, for the quantification of a protein using a mass spectrometer, although there have been findings on the preparation of a stable isotope-labeled protein having the same sequence as that of the protein to be quantified to use the stable isotope-labeled protein as an internal standard, there have been no findings on the evaluation of the efficiency of a pretreatment (Non-patent Document 1). For the evaluation of the efficiency of a pretreatment, a method using a certain purified protein already present in nature as a standard protein and one of its digested peptide fragments as an evaluation peptide has been carried out. However, the method has a problem that it affects the quantitative value and performs an overestimation when a protein partially having the same amino acid sequence as that of the evaluation peptide is present in a measurement sample. In addition, in the case of evaluation using one evaluation peptide, there is a possibility that the evaluation peptide is completely cut even when digestion does not sufficiently take place on the whole, posing a problem of overestimating the pretreatment efficiency.

There is a method which involves preparing an artificial protein labeled with a stable isotope by producing an artificial protein in which a target digested peptide used for the quantification of each protein is incorporated and culturing *Escherichia coli* in a medium containing an amino acid labeled with a stable isotope. A method is reported which involves adding the artificial protein labeled with a stable isotope to a protein to be quantified, pretreating the mixture, measuring the peak area ratio (of the non-labeled target digested peptide/the stable isotope-labeled target digested peptide) using a mass spectrometer, and calculating the relative expression ratio of each protein corrected for the pretreatment efficiency from the peak area ratio (Non-patent Document 2). However, this method limits the target protein to be quantified, requires that the artificial protein be redesigned and repurified after each change of the target protein, and therefore has a large problem in general versatility.

PRIOR ART DOCUMENTS

Patent Documents

Patent Document 1: Japanese Patent Laid-Open No. 2004-28993
Patent Document 2: Japanese Patent Laid-Open No. 2004-77276
Patent Document 3: National Publication of International Patent Application No. 2004-533610
Patent Document 4: International Publication No. WO07/055116
Patent Document 5: Japanese Patent Application No. 2008-251212

Non-Patent Documents

Non-patent Document 1: Dupius K. et al., Proteomics 2008, 8: 4633-4636
Non-patent Document 2: Kito K. et al., J. Proteome Res. 6: 792-800, 2007

SUMMARY OF THE INVENTION

Object to be Solved by the Invention

An object of the present invention is to provide an evaluation peptide high in reliability and general versatility for evaluating the pretreatment efficiency in the quantification of a protein using a mass spectrometer, an artificial standard protein comprising the evaluation peptide, and a method for quantifying a protein using the artificial standard protein.

Means to Solve the Object

In intensive studies for solving the above-described problems, the present inventors have obtained the finding that a peptide having the absence of the same amino acid sequence as that in a known protein and capable of being detected with a sufficient sensitivity by a mass spectrometer can be used as an evaluation peptide for versatile application to samples of all species of proteins. In addition, the present inventors have found the number of amino acid residues and amino acid species of a peptide suitable for detection by a mass spectrometer, studied specific peptides, and designed 4 types of amino acid sequences of evaluation peptides satisfying the above requirements.

The finding has also been obtained that the incorporation of 2 or more of each of 2 types or more of evaluation peptides into an artificial standard protein enables the evaluation that a protein has been completely digested by a protein-digesting enzyme and additionally increases sensitivity per protein. In addition, the finding has been obtained that the insertion of 2 or more cysteines into an artificial standard protein enables the evaluation of the modification by which a S—S bond having a significant effect on digestion efficiency is dissociated. The present invention has been accomplished based on these findings.

Thus, the present invention relates to [1] a method comprising: selecting a peptide consisting of an amino acid sequence which is not identical to that in a naturally occurring protein and a variant thereof and is capable of being detected by mass spectrometry and containing an amino acid recognized by a protein-digesting enzyme; and using the peptide as an evaluation peptide for quantifying a protein using a mass spectrometer and [2] the method according to [1] above, wherein the amino acid sequence which is not identical to that in a naturally occurring protein and a variant thereof is an amino acid sequence which is not identical to that in a known protein.

The present invention also relates to [3] an evaluation peptide for quantifying a protein using a mass spectrometer, the peptide being a peptide having 3 to 20 amino acid residues, having an amino acid recognized by a protein-digesting enzyme at the C-terminus, not having the amino acid recognized by the protein-digesting enzyme in any region other than the C-terminus, and consisting of an amino acid sequence which is not identical to that in a naturally occurring protein and a variant thereof, [4] the evaluation peptide according to [3] above, wherein the peptide has an amino acid capable of being labeled with a stable isotope, [5] the evaluation peptide according to [3] or [4] above, wherein the peptide has 8, 10 or 12 amino acid residues, contains proline or glycine, and does not contain histidine, [6] the evaluation peptide according to [5] above, wherein the peptide contains 1 or 2 prolines, and [7] an evaluation peptide for quantifying a protein using a mass spectrometer, the peptide being composed of any of the amino acid sequences shown in the following (1) to (4): (1) VGAPGV-PALK (SEQ ID NO: 1); (2) QIGDPTVPSGVK (SEQ ID NO: 2); (3) DAPGSGLK (SEQ ID NO: 3); and (4) NVA-PAGPTLK (SEQ ID NO: 4).

The present invention further relates to [8] a method for using the evaluation peptide according to any one of [3] to [7] above for the quantification of a protein using a mass spectrometer.

The present invention also relates to [9] an artificial standard protein for a quantification of a protein using a mass spectrometer, comprising 2 or more types of amino acid sequences for the evaluation peptide according to any one of [3] to [7] above, each type of the sequences contained at 2 or more locations, and [10] the artificial standard protein according to [9] above, wherein the artificial standard protein has 2 or more cysteines per molecule.

In addition, the present invention relates to [11] a method for using the artificial standard protein according to [9] or [10] above as an artificial standard protein for the quantification of a protein using a mass spectrometer, and [12] a method for quantifying a protein, using the artificial standard protein according to [9] or [10] above as an artificial standard protein for the quantification of a protein using a mass spectrometer.

Further, the present invention relates to [13] a method for quantifying a protein, successively comprising the steps of the following (a) to (c): (a) adding an artificial standard protein of known mass to a sample comprising a protein to be quantified, further adding a protein-digesting enzyme thereto, and digesting the protein to be quantified and the artificial standard protein; (b) adding peptides labeled with a stable isotopes, having the same sequences as those of the peptides that are the digestion products of the protein to be quantified and the artificial standard protein to the sample obtained in the step (a) and performing a liquid chromatograph-tandem mass spectrometry (LC-MS/MS) measurement; and (c) calculating the ratio between the mass of the artificial standard protein added in the step (a) and the mass of each of the peptides that are the digestion product of the artificial standard protein obtained by the measurement in the step (b) to evaluate the efficiency of treatment with the protein-digesting enzyme; and [14] a standard substance kit for quantifying a protein using a mass spectrometer, comprising the following (A) to (C): (A) the artificial standard protein according to [9] or [10] above; (B) a protein-digesting enzyme; and (C) peptides labeled with a stable isotope, having the same sequences as those of peptides that are the digestion products of the artificial standard protein by the protein-digesting enzyme.

Effect of the Invention

The evaluation peptide of the present invention has high general versatility and the peptide can be used to evaluate the efficiency of a pretreatment of any measurement sample, enabling the reliability of protein quantitative values to be secured. The artificial standard protein having 2 or more of each of 2 types or more evaluation peptides incorporated therein enables the evaluation of the completeness of digestion which is very important for quantification in the point that the recovery rate of all of the evaluation peptides is 100% when it is completely fragmented by a protein-digesting enzyme. The evaluation peptide of the present invention is a peptide having the absence of the same amino acid sequence as that in a known protein and capable of being detected with a sufficient sensitivity by a mass spectrometer, and has such a high general versatility that it can be applied to any protein samples.

BRIEF DESCRIPTION OF DRAWINGS

FIG. 3 is an amino acid sequence of the produced artificial standard protein and a schematic diagram thereof (SEQ ID NO: 5). The underlined portions are inserted evaluation peptides; * indicates an amino acid labeled with a stable isotope.

FIG. 4-1 is a chromatogram of an evaluation peptide (VGAPGVPALK; SEQ ID NO: 1) for the calibration curve 10 fmol.

FIG. 4-2 is a chromatogram of an evaluation peptide (QIGDPTVPSGVK; SEQ ID NO: 2) for the calibration curve 10 fmol.

FIG. 4-3 is a chromatogram of an evaluation peptide (DAPGSGLK; SEQ ID NO: 3) for the calibration curve 10 fmol.

FIG. 4-4 is a chromatogram of an evaluation peptide (NVAPAGPTLK; SEQ ID NO: 4) for the calibration curve 10 fmol.

Figure 1:
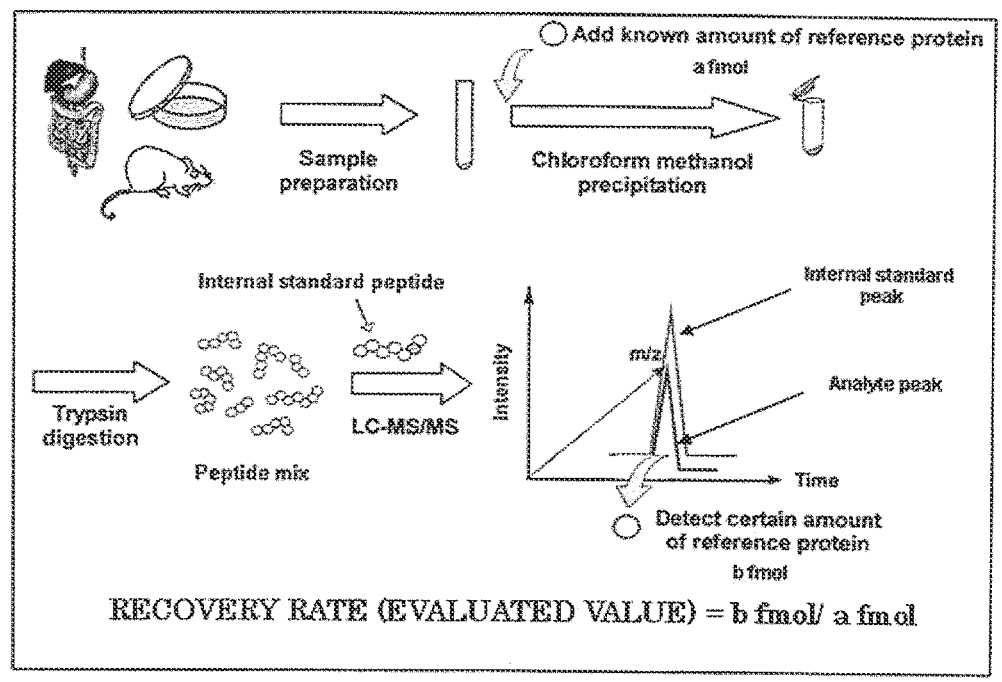
FIG. 1 is a schematic flow of pretreatment evaluation in the protein quantification of the present invention.

MODE FOR CARRYING OUT THE INVENTION (Evaluation Peptide)

The present invention is not particularly limited provided that it is a method comprising: selecting a peptide consisting of an amino acid sequence which is not identical to that in a naturally occurring protein and a variant thereof and is capable of being detected by mass spectrometry and containing an amino acid recognized by a protein-digesting enzyme; and using the peptide as an evaluation peptide for quantifying a protein employing a mass spectrometer. Examples of the amino acid sequence which is not identical to that in any naturally occurring protein and a variant thereof can include an amino acid sequence which is not identical to that in an unknown or known protein; however, more preferred is an amino acid sequence which is not identical to that in a known protein. Preferred examples of the amino acid sequence which is not identical to that in a known protein can include an amino acid sequence as which the same amino acid sequence is not confirmed to be present by a homology search using a data base such as Swiss-Prot.

The naturally occurring proteins include a homologous protein (homolog) and a protein having an SNP-derived varied site. Examples of the variant of a naturally occurring protein can include a protein consisting of an amino acid sequence in which one or a plurality of amino acids are deleted, substituted, or added in the amino acid sequence of the naturally occurring protein; more specific examples thereof can include a protein consisting of an amino acid sequence in which one or several amino acids are deleted, substituted, or added.

Specific examples of the amino acid sequence capable of being detected by a mass spectrometer include an amino acid sequence constituting a peptide capable of being detected by LC-MS/MS; more specifically, an amino acid sequence constituting a peptide of which 10 fmol can be detected by LC-MS/MS is preferable. The phrase "10 fmol can be detected by LC-MS/MS" refers to "10 fmol can be detected, for example, using LC-MS/MS System "API5000 (trade name)", "4000Q TRAP (trademark)", or the like from Applied Biosystems".

The phrase "containing an amino acid recognized by a protein-digesting enzyme" means "containing an amino acid which is recognized by a protein-digesting enzyme and provides a cleavage site". The protein-digesting enzyme is preferably an endopeptidase; examples thereof include trypsin. In the amino acid sequence of the evaluation peptide of the present applied invention, the site recognized by a protein-digesting enzyme is preferably the C-terminus of the amino acid sequence and preferably has an amino acid recognized by the protein-digesting enzyme in the region except the C-terminus. For example, when trypsin is used as a protein-digesting enzyme, the evaluation peptide preferably has lysine (K) or arginine (R) at the C-terminus.

The evaluation peptide has an amino acid capable of being labeled with a stable isotope; examples of the amino acid capable of being labeled with a stable isotope can include leucine (L) and valine (V). One evaluation peptide may have an amino acid capable of being labeled with a stable isotope in one site or a plurality of sites thereof. The number of types of amino acids capable of being labeled with a stable isotope may be one or plural; however, one type is preferable in view of cost or the like during practice.

The number of the amino acid residues of the evaluation peptide is not particularly limited; however, it is preferably 4 to 30, more preferably 5 to 15, still more preferably 8 to 12. Particularly, it is preferable that the evaluation peptide has 8, 10, or 12 amino acid residues, contains proline (P) and/or glycine (G), and does not contain histidine (H); among others, preferred is one containing 1 or 2 prolines.

The peptide having 8, 10, or 12 amino acid residues, containing proline and/or glycine, and not containing histidine is suitable as an evaluation peptide since it can be detected in a smaller amount for its presence because of giving a strong signal in mass spectrometry.

The sequence of the evaluation peptide of the present invention can be designed by combining the above conditions and known criteria. As known criteria, for example, criteria for selecting a peptide suitable for the analysis of a protein using a mass spectrometer (e.g., criteria as described in WO2007/055116) can be combined.

Specifically, for example, 1 or 2 or more of the criteria can be used including:
 a peptide obtained using trypsin degradation enzyme;
 a peptide, as content conditions of a hydrophobic amino acid consisting of tryptophan, tyrosine, valine, leucine, isoleucine, or phenylalanine and sequence conditions, having a hydrophobic amino acid content of 80% or less, preferably 50% or less and not having 10 or more consecutive such hydrophobic amino acids;
 a peptide, as specific amino acid sequence conditions, not containing the sequence asparagine-X-Y (where X represents an amino acid other than proline and Y represents serine, threonine or cysteine);

a peptide whose protease cleavage site is not arginine-arginine, arginine-lysine, lysine-arginine, or lysine-lysine;

a peptide not containing methionine or cysteine; and a peptide not containing tryptophan or glutamic acid. A score can also be set to each of these criteria to design a peptide having a high total score.

Specific examples of the evaluation peptide include peptides composed of amino acid sequences shown in SEQ ID NOs: 1 to 4.

(Artificial Standard Protein)

The above evaluation peptide can be used to design an artificial standard protein; the present invention also relates to an artificial standard protein comprising 2 or more of each of 2 or more types of amino acid sequences for the evaluation peptide. Herein, the number of each evaluation peptide incorporated in an artificial standard protein is called "the incorporation number".

In the artificial standard protein, a plurality of types of evaluation peptides (for example, A, B, C, and D) may be randomly incorporated together with a plurality of types of non-evaluation peptide moieties (X) (for example, A-B-X-B-C-B-X-A-B-C-A-X) or may be arranged in order together therewith (for example, X-A-X-B-X-A-B-X-A-B-X-A-B); however, it is preferably designed by arranging 4 types or more evaluation peptides in order (A-B-C-D), which is then repeated (A-B-C-D-X-A-B-X-C-D; the incorporation number is 2). When the non-evaluation peptide moiety (X) is used, it is necessary in separating an evaluation peptide using a protein-digesting enzyme to use an amino acid recognized by the protein-digesting enzyme at its C-terminus.

Because the artificial standard protein has 2 or more of each of 2 types or more evaluation peptides, the complete digestion of a protein by a protein-digesting enzyme can be evaluated, and, in addition, sensitivity per protein is high. Thus, the artificial standard protein can be preferably used as an artificial standard protein for quantifying a protein using a mass spectrometer.

The artificial standard protein more preferably has 2 or more cysteines (S). These cysteines (S) may be incorporated in the amino acid sequence of the evaluation peptide or in a region other than the evaluation peptide; however, preferred is a region other than the evaluation peptide (the region of the above non-evaluation peptide moiety X).

The artificial standard protein may also have sequences other than the evaluation peptide moiety, for example, a transport signal sequence and a tag sequence for purification, and preferably contains a tag sequence for purification.

The artificial standard protein can be produced, for example, by the following method. That is, a cDNA sequence is designed from the amino acid sequence of the above artificial standard protein and synthesized by nucleic acid oligo synthesis, PCR, or the like. In addition, the cDNA is incorporated into an expression vector, and a protein is synthesized using *Escherichia coli* or the like. The resultant synthetic protein can be purified using known conditions and method such as a purification method using a tag sequence. The precise amount (concentration) of the purified artificial standard protein can be calculated by amino acid analysis.

(Pretreatment Evaluation and Quantification of Protein Using Artificial Standard Protein)

For the pretreatment evaluation and quantification of a protein to be quantified using the artificial standard protein of the present invention, a peptide labeled with a stable isotope having the same sequence as that of an evaluation peptide is synthesized in advance for the quantification of the absolute amount of the evaluation peptide. The stable isotope-labeled peptide added as an internal standard is labeled with at least one stable isotope of 15N, 13C, 18O, and 2H. In the LC-MS/MS measurement, the non-labeled evaluation peptide and the stable isotope-labeled evaluation peptide as an internal standard are separated by the mass difference therebetween; thus, the mass difference enabling separation by LC-MS/MS is necessary. A peptide containing leucine (L) whose 6 positions are labeled with 13C is preferably used. The stable isotope-labeled peptide needs to have at least one amino acid labeled with a stable isotope, and the peptide can be prepared by any method known to those of ordinary skill in the art. For example, an amino acid labeled with a stable isotope can be used to chemically synthesize a desired stable isotope-labeled peptide by a suitable means such as an F-moc method (Amblard M, Fehrentz J. A., Martinez J., Subra G. Methods Mol. Biol. 298: 3-24 (2005)). The stable isotope-labeled peptide thus obtained and the peptide to be quantified are chemically the same except that they are different in the mass of the labeled amino acid and show the same behavior in the LC-MS/MS measurement; the loss degrees of the analyte and the standard are identical.

In the protein quantification according to the present invention, a known amount, preferably 100 to 10,000 fmol, of an artificial standard protein is added to a protein sample comprising a protein to be quantified before pretreatment, to which a protein-digesting enzyme is then added to perform a pretreatment (step (a)). The pretreatment refers to a treatment which involves adding a protein-digesting enzyme to digest an artificial standard protein and a protein to be quantified to make peptides. The protein-digesting enzyme used may be the above-described trypsin or the like. The temperature and time of the pretreatment may use standard reaction conditions of the protein-digesting enzyme; for example, the pretreatment may be carried out at a temperature of 35° C. to 45° C. for 1 minute to 20 hours.

After pretreatment, a known amount of a stable isotope-labeled evaluation peptide is added to the sample obtained in the pretreatment step. The amount of the stable isotope-labeled evaluation peptide added may be a known amount; however, it is preferably an amount [mol] corresponding to (an artificial standard protein [mol]×the incorporation number).

Simultaneously, for the quantification of the protein to be quantified, a stable isotope-labeled peptide is also added which has the same sequence as that of a digestion product of the protein to be quantified obtained using the protein-digesting enzyme.

This sample is measured by liquid chromatograph-tandem mass spectrometry (LC-MS/MS), and concurrently with the quantification of the protein to be quantified, the absolute amount of each evaluation peptide is measured by a known internal standard method (e.g., a method as described in International Publication No. WO 07/055116) (step (b)).

The evaluated value of the pretreatment efficiency is calculated from the amount (A [mol]) of the artificial standard protein added and the quantitative value (B [mol]) of each evaluation peptide (step (c)).

The evaluated value is obtained from the following equation:

$$\text{Evaluated Value} = B/(A \times \text{Incorporation Number}).$$

Figure 2:
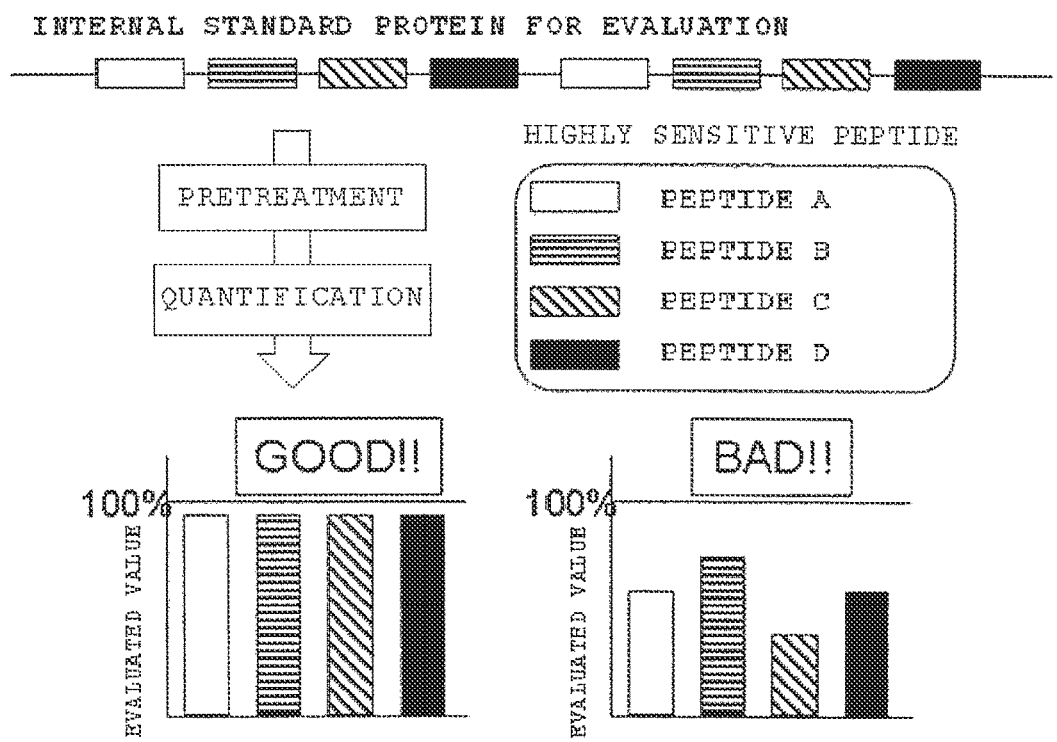
FIG. 2 is a schematic method for pretreatment evaluation in the protein quantification of the present invention.

When the evaluated values of the evaluation peptides are constant values and are 0.80 or more, preferably 0.90 or more, it is evaluated that the pretreatment has been sufficiently performed, and the reliable quantitative value of the protein to be quantified can be determined to have been obtained (see FIGS. 1 and 2).

Examples of "the evaluated values are constant values" include a case where the variation is small or absent between evaluated values for a plurality of types of evaluation peptides contained in an artificial standard protein, specifically the variation from the average value is within 0.10.

Examples of "the evaluated values are 0.80 or more" include a case where the average evaluated values for a plurality of types of evaluation peptides contained in an artificial standard protein are 0.80 or more.

In addition, the evaluated value of the pretreatment efficiency obtained in the preceding step can also be used to calculate the quantitative value of the protein to be quantified. An evaluated value of less than 0.8 poses a problem with the pretreatment; thus, remeasurement or changes in the measurement method, or the like may be considered without adopting the measured value.

The present invention also relates to a kit for quantifying a protein, and the kit of the present invention comprises the following (A) to (C):

(A) an artificial standard protein,
(B) a protein-digesting enzyme, and
(C) peptides labeled with a stable isotope, having the same sequences as those of peptides as digestion products of the artificial standard protein by the protein-digesting enzyme.

The artificial standard protein, the protein-digesting enzyme, and the peptide labeled with a stable isotope, having the same sequence as that of the peptide as the digestion product of the artificial standard protein by the protein-digesting enzyme contained in the kit are the same as those described in detail above; the kit of the present invention may also comprise a buffer solution, a pH adjuster, a reaction container, and the like in addition to the above (A) to (C), according to the need and purpose.

The present invention will be more specifically described below with reference to Examples. However, these Examples are not intended to limit the technical scope of the present invention.

EXAMPLES

Example 1

Figures 3, 4:
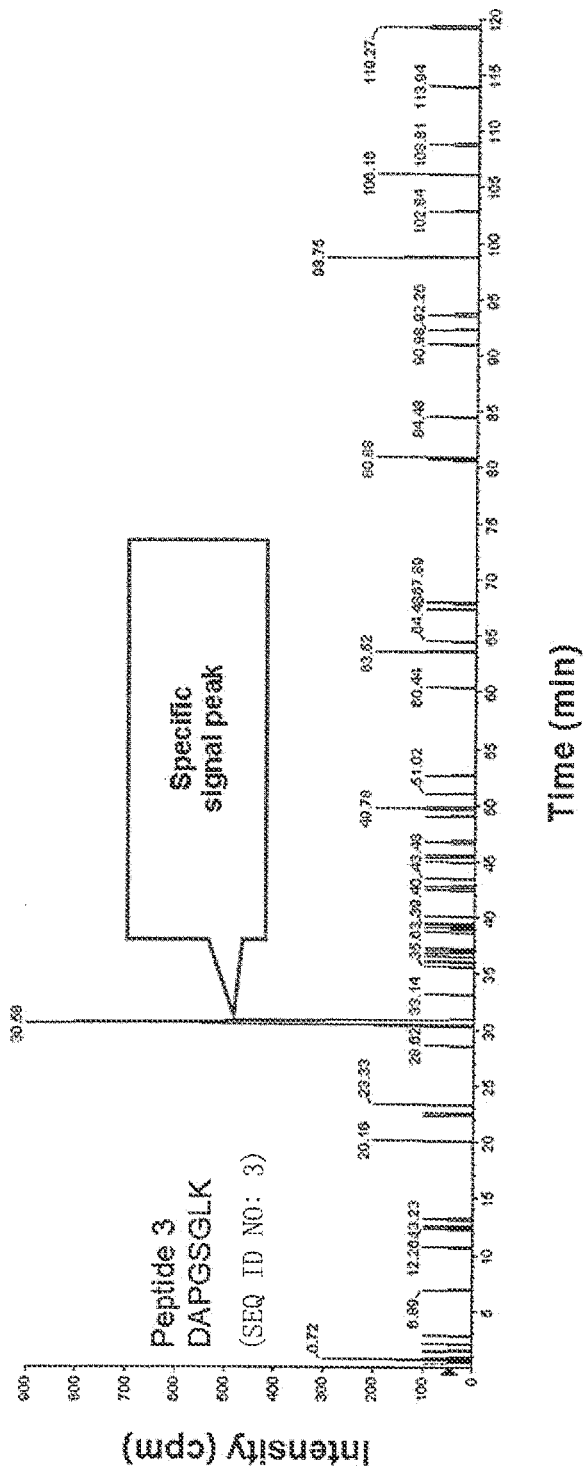
Figure 4:
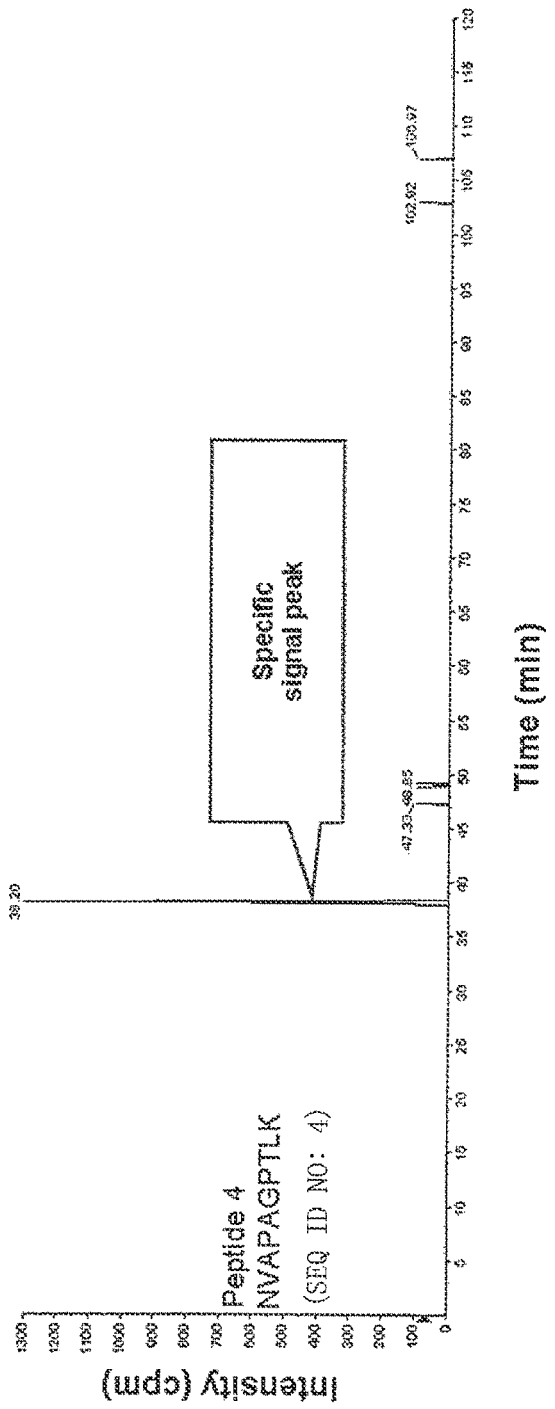

Preparation of Artificial Standard Protein Comprising Evaluation Peptide and Confirmation of Sensitivity of Evaluation Peptide VGAPGVPALK (SEQ ID NO: 1), QIGDPTVPSGVK (SEQ ID NO: 2), DAPGSGLK (SEQ ID NO: 3), and NVAPAGPTLK (SEQ ID NO: 4) were selected as evaluation peptides, and an artificial standard protein (SEQ ID NO: 5) containing 2 each of these types of peptides was prepared (see FIG. 3). The artificial standard protein was prepared according to the following method.

1. IPTG Induction

*Escherichia coli* (BL21-CodonPlus (DE3)-RIPL) transformed with a pET-vector having artificial standard protein cDNA inserted was shake cultured overnight in a LB medium containing 30 mg/L of kanamycin and 50 mg/L of chloramphenicol, diluted in the LB medium, and cultured until OD600 reaches a value of around 0.4. IPTG at a final concentration of 100 mM was added thereto, which was further incubated for 3 hours to induce the expression of the protein. The *E. coli* after inducing the expression was subjected to ultrasonic breaking in the presence of 8 M Urea to prepare a soluble fraction and an insoluble fraction, followed by fractionation using SDS-PAGE for detection employing CBB R-250.

2. Purification of Artificial Standard Protein

The *E. coli* soluble fraction was added to a spin column packed with cobalt resin; the column was washed with a 10 mM imidazole solution; and the artificial standard protein was eluted using 50 mM, 150 mM and 500 mM imidazole solutions.

(Confirmation of Sensitivity of Evaluation Peptide)

Peaks were confirmed to be detected at 10 fmol for all of the 4 types of evaluation peptides inserted in the artificial standard protein. The confirmation was carried out by the following method.

The 4 types of evaluation peptides VGAPGVPALK (SEQ ID NO: 1), QIGDPTVPSGVK (SEQ ID NO: 2), DAPGSGLK (SEQ ID NO: 3), and NVAPAGPTLK (SEQ ID NO: 4) were mixed, and quantified using the MRM mode of LC-MS/MS under the following conditions:

Column: Agilent 300SB-C18 0.5 mm ID×150 mm, 5 μm particles
HPLC: Agilent 1100 system
Mass Spectrometer: API5000
Gradient Condition: 1 to 45% acetonitrile/0.1% formic acid, 50 μL/min, 50 min.

The results are shown in FIG. 4-1 to FIG. 4-4. As shown in FIG. 4-1 to FIG. 4-4, prominent peaks were confirmed for the 4 types of evaluation peptides VGAPGVPALK (SEQ ID NO: 1), QIGDPTVPSGVK (SEQ ID NO: 2), DAPGSGLK (SEQ ID NO: 3), and NVAPAGPTLK (SEQ ID NO: 4), and it was shown that they can be detected even at 10 fmol.

Example 2

Evaluation 1 of Pretreatment Efficiency Using Evaluation Peptide

The pretreatment efficiency in the quantification of a protein was evaluated using the artificial standard protein of Example 1. A sample for evaluation was prepared and evaluated by the following method. The sample for evaluation was handled by a person not familiarized with the experimental procedure.

1. Preparation of Peptide Sample 10,000 fmol of an artificial standard protein and 2,200 fmol of *E. coli*-derived Triose Phosphate Isomerase (TPI) as a reference example were added to 50 μg of a kidney plasma membrane sample isolated from mice. Then, the mixture was denatured using a 7 M guanidine hydrochloride solution (dissolved in 0.1 M Tris-HCl, 10 mM EDTA pH 8.5) and subjected to reduction treatment with DTT and carbamide methylation treatment with iodoacetamide to protect the SH group of a cysteine residue. Subsequently, the resultant was desalted and concentrated by a methanol-chloroform precipitation method and resuspended in 1.2 M Urea/10 mM Tris-HCl. Thereafter, trypsin was added thereto in an amount of 1/100 the weight of protein for enzymatic digestion at 37° C. for 16 hours to provide peptide samples.

2. Quantitative Analysis of Peptide Sample 500 fmol of 13C6, 15N-labeled peptides were added to the above peptide samples, which was then measured by LC-MS/MS. After measurement, the MS spectrum area ratio between peaks of each peptide to be quantified and each corresponding 13C6, 15N-labeled peptide was calculated, and a quantitative value was calculated using a calibration curve.

3. Preparation of Calibration Curve

A calibration curve was prepared using a selected peptide to be quantified. Specifically, 500 fmol of a 13C6, 15N-labeled peptide was added to 10 fmol, 50 fmol, 100 fmol, 500 fmol and 1,000 fmol of the non-labeled peptide, which were then measured by LC-MS/MS to calculate MS spectrum area ratios (non-labeled peptide/13C6, 15N-labeled peptide) to prepare a calibration curve.

Figure 5:
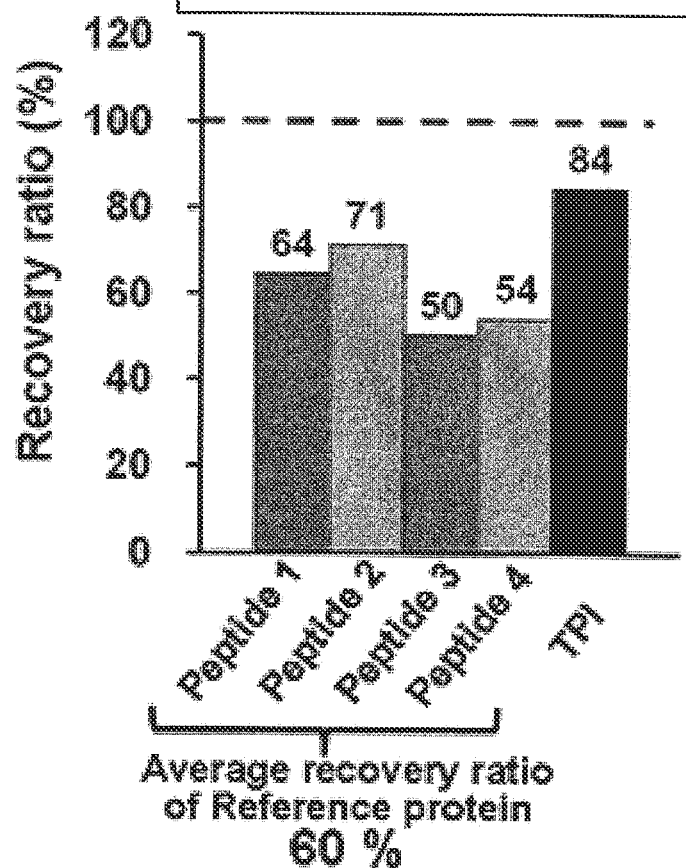
FIG. 5 is a graph showing the results of the evaluation of the pretreatment efficiency when the pretreatment is performed by a person not familiarized with the experimental procedure. The evaluation value was variable among the 4 different evaluation peptides and each peptide had a low value.

The results are shown in FIG. 5. It was determined from FIG. 5 that the protein in this experiment had been not suitably pretreated because the evaluated values of the evaluation peptides were 50 to 71% and therefore variable and all of the values were low. The evaluated value of TPI as a reference example was 84%, showing that the validity of the pretreatment could not properly be determined only from that of TPI.

Example 3

Evaluation 2 of Pretreatment Efficiency Using Evaluation Peptide

The pretreatment efficiency was evaluated in the same way as in Example 2. However, the sample for evaluation was handled by a person familiarized with the experimental procedure. The addition amount of the artificial standard protein was 250 fmol, and the addition amount of *E. coli*-derived Triose Phosphate Isomerase (TPI) was 700 fmol.

Figure 6:
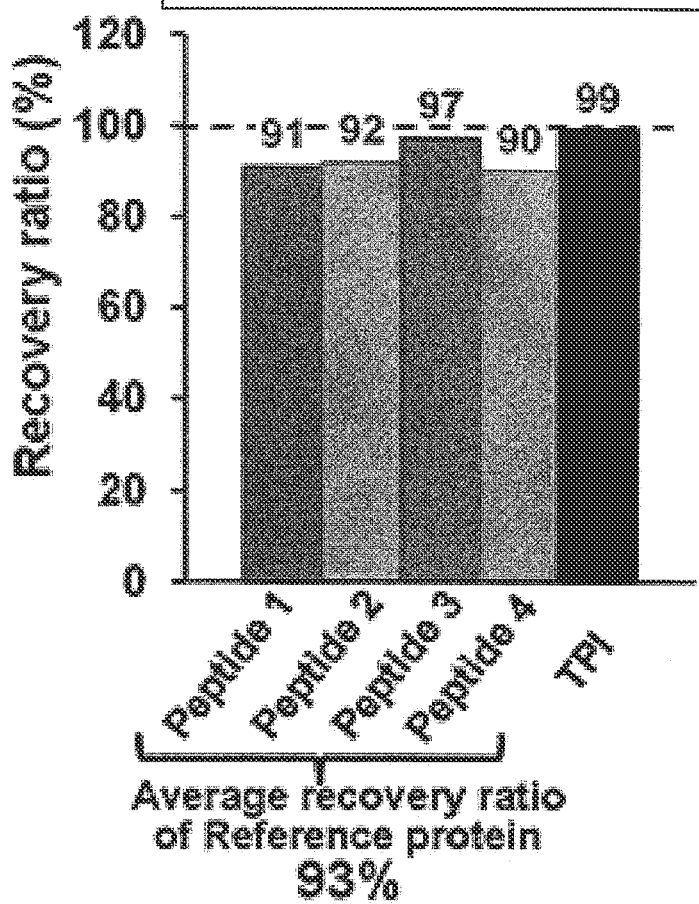
FIG. 6 is a graph showing the results of the evaluation of the pretreatment efficiency when the pretreatment is performed by a person familiarized with the experimental procedure. The evaluation value was less variable among the 4 different evaluation peptides and each peptide had a high value.

The results are shown in FIG. 6. As shown in FIG. 6, the evaluated values of the evaluation peptides were 90 to 97% and therefore less variable, and all of the values were high. The recovery rate of TPI as a control for the pretreatment was 99%, and the protein in this experiment for which the evaluation peptides had high evaluated values was determined to have been suitably pretreated. In FIG. 6 in which the evaluated values were high, TPI had a high recovery rate compared to that in FIG. 5 in which the evaluated values were low (FIG. 6: 99%, FIG. 5: 84%), and a correlation was therefore observed between the evaluated value and the recovery rate, showing the efficacy of the pretreatment evaluation using the evaluation peptides.

Reference Example 1

Selection of More Preferable Evaluation Peptide

Figure 7:
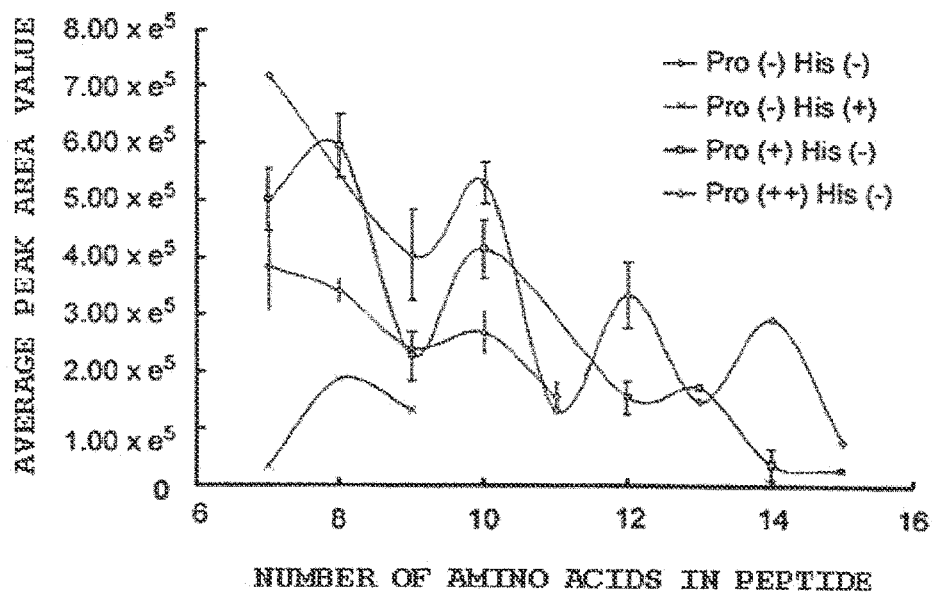
FIG. 7 is a graph showing a plot of average peak area values and peptide lengths after analyzing 83 types of peptides in the MRM mode of LC-MS/MS. A higher content of proline (P) increases the average peak area value. This figure shows that the presence of histidine (H) decreases the average peak area value.
Figure 8:
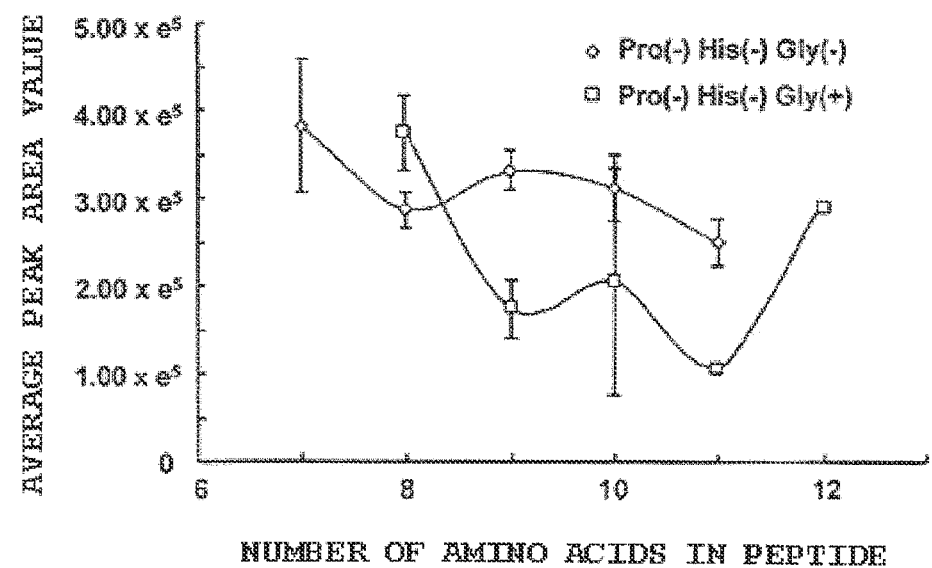
FIG. 8 is a graph showing the same plot after measurement as in FIG. 7. This figure shows that a higher content of glycine increases the average peak area value.

Average peak area values were plotted against peptide lengths after analyzing 83 types of peptides (500 fmol each) in the MRM mode of LC-MS/MS (ABI4000QTRAP). As a result, as shown in FIG. 7, a higher content of a proline (P) residue increases the average peak area value. The presence of histidine (H) decreases the average peak area value. As shown in FIG. 8, a higher content of a glycine residue increases the average peak area value.

The above results showed that the evaluation peptide having 8, 10, or 12 amino acid residues, having proline or glycine, and not having histidine could be suitably detected by LC-MS/MS.

The invention claimed is:

1. An evaluation peptide for quantification of a protein using a mass spectrometer, the peptide being composed of any of the amino acid sequences shown in the following (1) to (4):

```
(1) VGAPGVPALK;      (SEQ ID NO: 1)

(2) QIGDPTVPSGVK;   (SEQ ID NO: 2)

(3) DAPGSGLK;       (SEQ ID NO: 3)
and (4) NVAPAGPTLK.     (SEQ ID NO: 4)
```

2. An artificial standard protein for quantification of a protein using a mass spectrometer, said artificial standard protein comprising 2 or more of each type of amino acid sequence of an evaluation peptide for quantifying a protein using a mass spectrometer, the peptide having 5 to 15 amino acid residues and consisting of an amino acid sequence containing proline and glycine and not containing histidine, tryptophan, or glutamine; the peptide amino acid sequence having an amino acid recognized by a protein-digesting enzyme at the C-terminus and not having the amino acid recognized by the protein-digesting enzyme in any region other than the C-terminus, the peptide amino acid sequence being not identical to any amino acid sequence of the same length in any known naturally occurring protein; wherein the 2 or more of each type of amino acid sequence of the evaluation peptide are separated within the artificial standard protein.

3. The artificial standard protein according to claim 2, wherein the artificial standard protein has 2 or more cysteines per molecule.

4. A method for protein quantification by mass spectrometry, comprising: adding the artificial standard protein according to claim 2 to a sample comprising a protein to be quantified using a mass spectrometer; and
quantifying the protein in the presence of the artificial standard protein using a mass spectrometer.

5. A method for quantifying a protein, successively comprising the steps of the following (a) to (c):
(a) adding the artificial standard protein according to claim 2 to a sample comprising a protein to be quantified, further adding a protein-digesting enzyme thereto, and digesting the protein to be quantified and the artificial standard protein;
(b) adding peptides labeled with a stable isotope, having the same sequences as those of the peptides that are the digestion products of the protein to be quantified and the artificial standard protein to the sample obtained in the step (a) and performing a liquid chromatograph-tandem mass spectrometry (LC-MS/MS) measurement; and
(c) calculating the ratio between the mass of the artificial standard protein added in the step (a) and the mass of each of the peptides that are the digestion product of the artificial standard protein obtained by the measurement in the step (b) to evaluate the efficiency of treatment with the protein-digesting enzyme.

6. A standard substance kit for quantifying a protein using a mass spectrometer, comprising the following (A) to (C):
(A) the artificial standard protein according to claim 2;
(B) a protein-digesting enzyme; and
(C) peptides labeled with a stable isotope, said peptides having the same sequences as those of peptides that are the digestion products of the artificial standard protein digested by the protein-digesting enzyme.

* * * * *

SEQUENCE LISTING

```
<160> NUMBER OF SEQ ID NOS: 5

<210> SEQ ID NO 1
<211> LENGTH: 10
<212> TYPE: PRT
<213> ORGANISM: artificial
<220> FEATURE:
<223> OTHER INFORMATION: monitoring peptide1 (evaluation peptide1)

<400> SEQUENCE: 1

Val Gly Ala Pro Gly Val Pro Ala Leu Lys
1               5                   10

<210> SEQ ID NO 2
<211> LENGTH: 12
<212> TYPE: PRT
<213> ORGANISM: artificial
<220> FEATURE:
<223> OTHER INFORMATION: monitoring peptide2 (evaluation peptide2)

<400> SEQUENCE: 2

Gln Ile Gly Asp Pro Thr Val Pro Ser Gly Val Lys
1               5                   10

<210> SEQ ID NO 3
<211> LENGTH: 8
<212> TYPE: PRT
<213> ORGANISM: artificial
<220> FEATURE:
<223> OTHER INFORMATION: monitoring peptide3 (evaluation peptide3)

<400> SEQUENCE: 3

Asp Ala Pro Gly Ser Gly Leu Lys
1               5
```

-continued

<210> SEQ ID NO 4
<211> LENGTH: 10
<212> TYPE: PRT
<213> ORGANISM: artificial
<220> FEATURE:
<223> OTHER INFORMATION: monitoring peptide4 (evaluation peptide4)

<400> SEQUENCE: 4

Asn Val Ala Pro Ala Gly Pro Thr Leu Lys
1               5                   10

<210> SEQ ID NO 5
<211> LENGTH: 368
<212> TYPE: PRT
<213> ORGANISM: artificial
<220> FEATURE:
<223> OTHER INFORMATION: artificial monitoring protein (artificial
      standard protein)

<400> SEQUENCE: 5

Met Ala His His His His His His Ser Ala Ala Leu Glu Val Leu Phe
1               5                   10                  15

Gln Gly Pro Gly Tyr Gln Asp Pro Asn Ser Lys Val Gly Ala Pro Gly
                20                  25                  30

Val Pro Ala Leu Lys Asn Trp His Gln Ala Trp His Glu Cys Ala Arg
            35                  40                  45

His Asp Gln Gln Leu Val Thr Ile Glu Ser Ala Asp Lys Asn Asn Ala
        50                  55                  60

Ile Ile Asp Leu Val Lys Arg Val Val Gly Lys Ser His Asn Leu Trp
65                  70                  75                  80

Leu Gly Gly Asn Asp Glu Tyr Ser Ser Ser Arg Asp Tyr Gly Arg Pro
                85                  90                  95

Phe Phe Trp Ser Pro Thr Gly Gln Ala Phe Ser Phe Ala Tyr Trp Ser
            100                 105                 110

Glu Asn Asn Pro Asp Asn Tyr Lys His Gln Glu His Cys Val His Arg
        115                 120                 125

Gln Ile Gly Asp Pro Thr Val Pro Ser Gly Val Lys Val Pro Leu Gly
    130                 135                 140

Gln Gly Ala Lys His Ala Lys Gln Ser Leu Arg Asp Ala Pro Gly Ser
145                 150                 155                 160

Gly Leu Lys Gln Asn Ala Thr Gln Ile Ala Ile Gln Ile Met Glu
                165                 170                 175

Asn His Glu Lys Lys Ile Arg Asp Leu Lys Asn Val Ala Pro Ala Gly
            180                 185                 190

Pro Thr Leu Lys Val Asp Lys Val Gly Ala Pro Gly Val Pro Ala Leu
        195                 200                 205

Lys Asn Trp His Gln Ala Trp His Glu Cys Ala Arg His Asp Gln Gln
    210                 215                 220

Leu Val Thr Ile Glu Ser Ala Asp Lys Asn Asn Ala Ile Ile Asp Leu
225                 230                 235                 240

Val Lys Arg Val Val Gly Lys Ser His Asn Leu Trp Leu Gly Gly Asn
                245                 250                 255

Asp Glu Tyr Ser Ser Ser Arg Asp Tyr Gly Arg Pro Phe Phe Trp Ser
            260                 265                 270

Pro Thr Gly Gln Ala Phe Ser Phe Ala Tyr Trp Ser Glu Asn Asn Pro
        275                 280                 285

Asp Asn Tyr Lys His Gln Glu His Cys Val His Arg Gln Ile Gly Asp

|     | 290 |     |     | 295 |     |     | 300 |     |     |
|-----|-----|-----|-----|-----|-----|-----|-----|-----|-----|
| Pro | Thr | Val | Pro | Ser | Gly | Val | Lys | Val | Pro | Leu | Gly | Gln | Gly | Ala | Lys |
| 305 |     |     |     |     | 310 |     |     |     | 315 |     |     |     |     |     | 320 |
| His | Ala | Lys | Gln | Ser | Leu | Arg | Asp | Ala | Pro | Gly | Ser | Gly | Leu | Lys | Gln |
|     |     |     |     | 325 |     |     |     |     | 330 |     |     |     |     | 335 |     |
| Asn | Ala | Thr | Gln | Ile | Ala | Ile | Gln | Gln | Ile | Met | Glu | Asn | His | Glu | Lys |
|     |     |     | 340 |     |     |     |     | 345 |     |     |     |     | 350 |     |     |
| Lys | Ile | Arg | Asp | Leu | Lys | Asn | Val | Ala | Pro | Ala | Gly | Pro | Thr | Leu | Lys |
|     |     | 355 |     |     |     |     | 360 |     |     |     |     | 365 |     |     |     |